United States Patent
Cole

(10) Patent No.: US 7,884,938 B2
(45) Date of Patent: Feb. 8, 2011

(54) MULTIPLE BEAM WIDE BAND CRDS CAVITY SENSOR AND DETECTOR

(75) Inventor: Barrett E. Cole, Bloomington, MN (US)

(73) Assignee: Honeywell International Inc., Morristown, NJ (US)

( * ) Notice: Subject to any disclaimer, the term of this patent is extended or adjusted under 35 U.S.C. 154(b) by 204 days.

(21) Appl. No.: 12/361,765

(22) Filed: Jan. 29, 2009

(65) Prior Publication Data
US 2010/0188661 A1  Jul. 29, 2010

(51) Int. Cl.
G01N 21/00 (2006.01)

(52) U.S. Cl. .................. 356/437; 356/440

(58) Field of Classification Search ......... 356/432–444
See application file for complete search history.

(56) References Cited

U.S. PATENT DOCUMENTS

| | | | | |
|---|---|---|---|---|
| 5,835,231 | A | 11/1998 | Pipino | 356/440 |
| 6,084,682 | A * | 7/2000 | Zare et al. | 356/437 |
| 6,377,350 | B1 | 4/2002 | Paldus et al. | |
| 6,654,392 | B1 * | 11/2003 | Arbore et al. | 372/20 |
| 7,352,463 | B2 | 4/2008 | Bounaix | 356/437 |
| 7,369,242 | B2 | 6/2008 | Cole et al. | 356/436 |
| 7,663,756 | B2 * | 2/2010 | Cole | 356/437 |
| 2004/0107764 | A1 | 6/2004 | Yan | 73/23.37 |
| 2007/0133001 | A1 * | 6/2007 | Cox et al. | 356/437 |
| 2007/0216903 | A1 * | 9/2007 | Cole et al. | 356/437 |
| 2007/0242266 | A1 * | 10/2007 | Cole | 356/300 |
| 2008/0111993 | A1 * | 5/2008 | Miller | 356/437 |
| 2008/0151248 | A1 * | 6/2008 | Cole et al. | 356/437 |
| 2008/0239299 | A1 | 10/2008 | Cole | 356/128 |
| 2010/0014094 | A1 * | 1/2010 | Cole et al. | 356/480 |

OTHER PUBLICATIONS

European Search Report corresponding to European Application No. EP 10 15 1134, dated May 18, 2010.
Yabai He et al.: "Multi-species trace gas detection by rapidly swept cavity ringdown spectroscopy," CLEO '07, 2007 Conference on Lasers and Electro-Optics, May 5-11, 2007, Baltimore, Maryland, USA, OSA, Piscataway, New Jersey, USA, May 6, 2007, pp. 1-2; XP031231719; ISBN: 978-1-55752-834-6.

* cited by examiner

*Primary Examiner*—Hoa Q Pham
(74) *Attorney, Agent, or Firm*—Husch Blackwell LLP; Welsh Katz

(57) ABSTRACT

A common multi-gas ring down detector incorporates a cavity that has a piezoelectric mirror and at least two displaced mirrors to define two different transit paths in the cavity. The two paths intersect at the piezoelectric mirror at different angles. Two different laser beams having first and second different wavelengths, can be coupled to the cavity, at different times, by driving the piezoelectric mirror axially. Beam outputs can be evaluated to establish the presence of selected gases in the cavity.

20 Claims, 2 Drawing Sheets

SINGLE CRDS CAVITY FOR MULTIPLE GASES AT DIFFERENT WAVELENGTHS

MULTIPLE BEAM WIDE BAND CRDS CAVITY SENSOR AND DETECTOR

FIELD

The invention pertains to gas sensors, or detectors. More particularly, the invention pertains to cavity ring-down spectrometer (CRDS)-type sensors usable to detect multiple gases.

BACKGROUND

Various types of cavity ring down sensors/detectors are known. They have been found to be especially useful were very small amounts of contaminants or undesirable gases are to be detected. These include, for example, HF, HCl, and NH3.

Representative sensors/detectors include Cole published application 2007/0242266 A1 entitled "Cavity Ring-down Spectrometer Having Mirror Isolation" published Oct. 18, 2007, Cole published application 2008/0239299 A1 entitled "CRDS Mirror for Normal Incidence Fiber Optic Coupling" published Oct. 2, 2008, and Cole et al. U.S. Pat. No. 7,369,242 B2 entitled "Cavity Ring-down Spectrometer for Semiconductor Processing" issued May 6, 2008. The above are all owned by the Assignee hereof and are all incorporated by reference herein.

It is at times desirable to measure as many gases as possible using CRDS ring down technology but the absorption lines of gases of interest may not be very close together. This would typically entail using a number of different cavities to measure each gas(es) of interest with any one wavelength range using a tunable laser detector and mirrors designed to be highly reflective in the range of interest.

There is a need for sensors of the CRDS-type which can be used to detect the presence of multiple different gases. Preferably such units would be implementable in a cost-effective fashion so as to be less expensive than multiple separate detectors.

DETAILED DESCRIPTION

Figure 1:
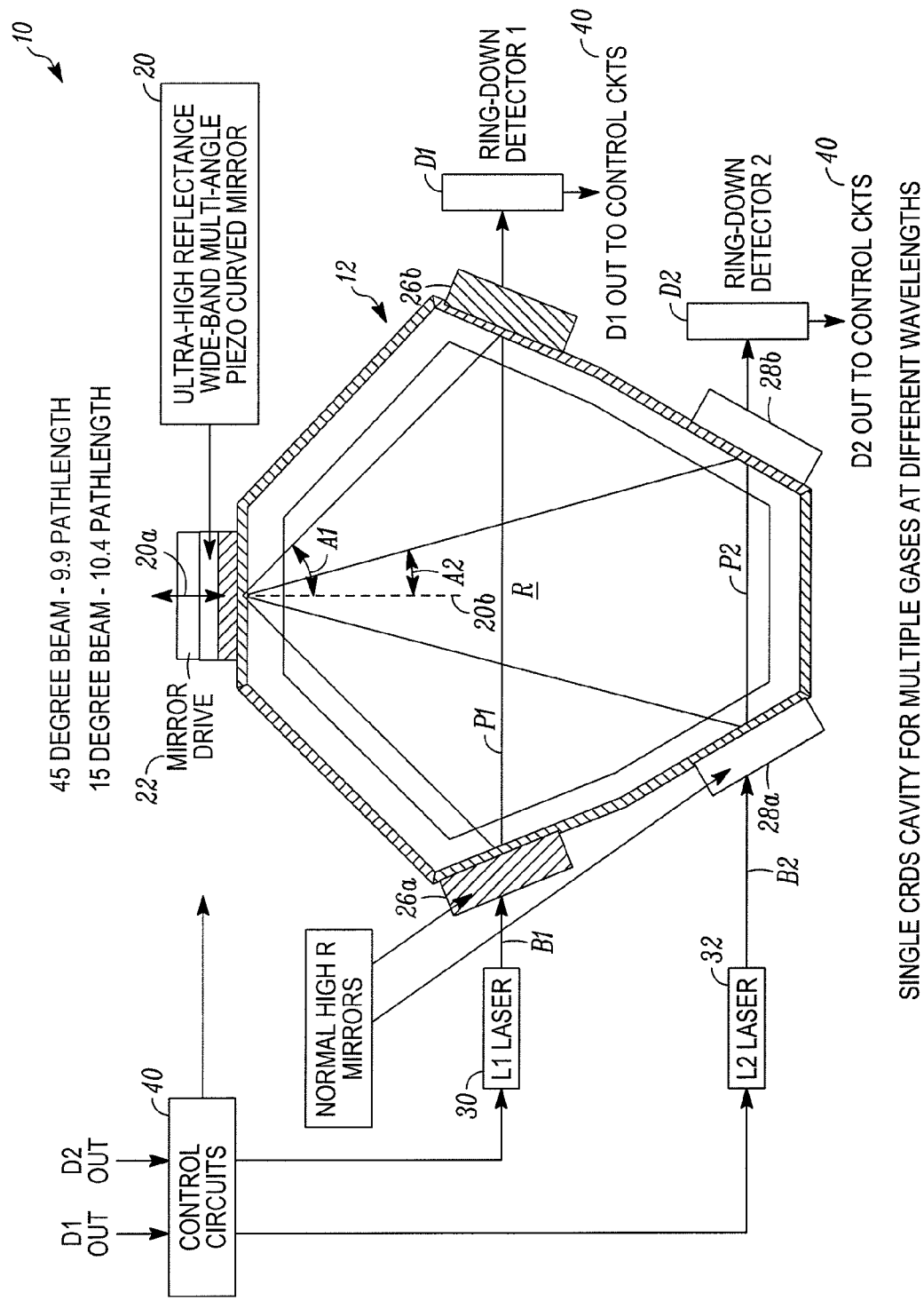
FIG. 1 is a top plan view of a multi-gas detector which embodies the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Embodiments of the invention are capable of measuring multiple different gases whose spectra are widely separated using one cavity. The cavity includes a pair of mirrors that exhibit high reflectance but only transmit within a fairly narrow band. These mirrors have transmission characteristics that make them desirable for light input and output using a single wavelength laser or a tunable laser.

One mirror is an ultra high reflectance piezoelectric mirror. By making this element more reflective by adding additional quarter wave pairs to the stack, it is possible to make this mirror substantially totally reflective over a very wide spectral range. Using a mirror of this type beams incident on the mirror from different angles will exhibit a reflectance that is shifted in wavelength. This is because the optical thickness of the layers is different at different angles. This characteristic can be used to implement two or more rings within a common cavity.

For the more normal beams, the reflectance is shifted to longer wavelengths. One embodiment of the invention will be capable of measuring three gases, such as HF, HCl, and NH3, with one cavity. The long wavelength HF spectra will be measured at more normal angles relative to the piezoelectric mirror. The HCl lines can be measured at intermediate angles and the short wavelength NH3 lines can be measured at more grazing incidence relative to the piezoelectric mirror.

By keeping the beam lengths approximately the same, it is also possible to use similar curved mirrors. These mirrors can be implemented as one of the side mirrors or also can be integrated into the piezoelectric mirror.

This CRDS cavity will preferably have input lasers that are tuned to the gas lines of interest. It will also preferably be made of a low expansion material such as glass. An internal center region will be open to gases flowing through it to allow for absorption of the radiation. The piezoelectric mirror will be movable so that the cavity can be coupled to multiple, such as two or three, laser beams for example.

Multiple lasers and detectors can be operated substantially simultaneously using the same piezoelectric mirror. Multiple beams will couple into the cavity at different times responsive to the motion of the piezoelectric mirror. Hence, the beams should not substantially interfere with each other in the cavity.

In another aspect of the invention, the curved mirror can be part of the piezoelectric mirror. Alternately, one or both of the two other mirrors can be curved.

FIG. 1 illustrates a detector 10 which embodies the invention. Detector 10 includes a CRDS-type sensor with a housing 12 which defines an internal cavity R through which a stream of gas can flow.

Housing 12 carries a piezoelectric mirror 20, which can be curved. It can be driven by unit 22 to exhibit reciprocal axial motion 20a.

Housing 12 carries high reflectance mirrors 26a,b and 28a,b. A fixed or tunable wavelength laser 30 emits a beam B1 of radiant energy of a wavelength that is absorbed by a first gas of interest in the cavity R. That beam of radiant energy B1 is coupled into the cavity R where it travels on a closed path P1.

A second laser 32 emits a beam of radiant energy B2 of a different wavelength that is absorbed by a second, different gas of interest in the cavity R. The second beam of radiant energy B2 travels on a different closed path P2 in the cavity R.

As will be understood by those of skill in the art, the circulating radiant energy beams on the paths P1, P2 are absorbed by the respective target gases, such as NH3, HCl or HF, and also emitted in part via respective mirrors 26b, 28b to impinge on detecting elements D1, or D2.

Outputs from D1, D2 can be coupled to control circuits 40 for evaluation. Control circuits 40 are in-turn coupled to drive unit 22 and piezoelectric mirror 20. Mirror 20 is driven and moves so that two (or more) laser beams B1, B2 can be coupled to the cavity R at different times. The lasers 30, 32 can thus be operated simultaneously without interfering with each other in the cavity.

Figure 2:
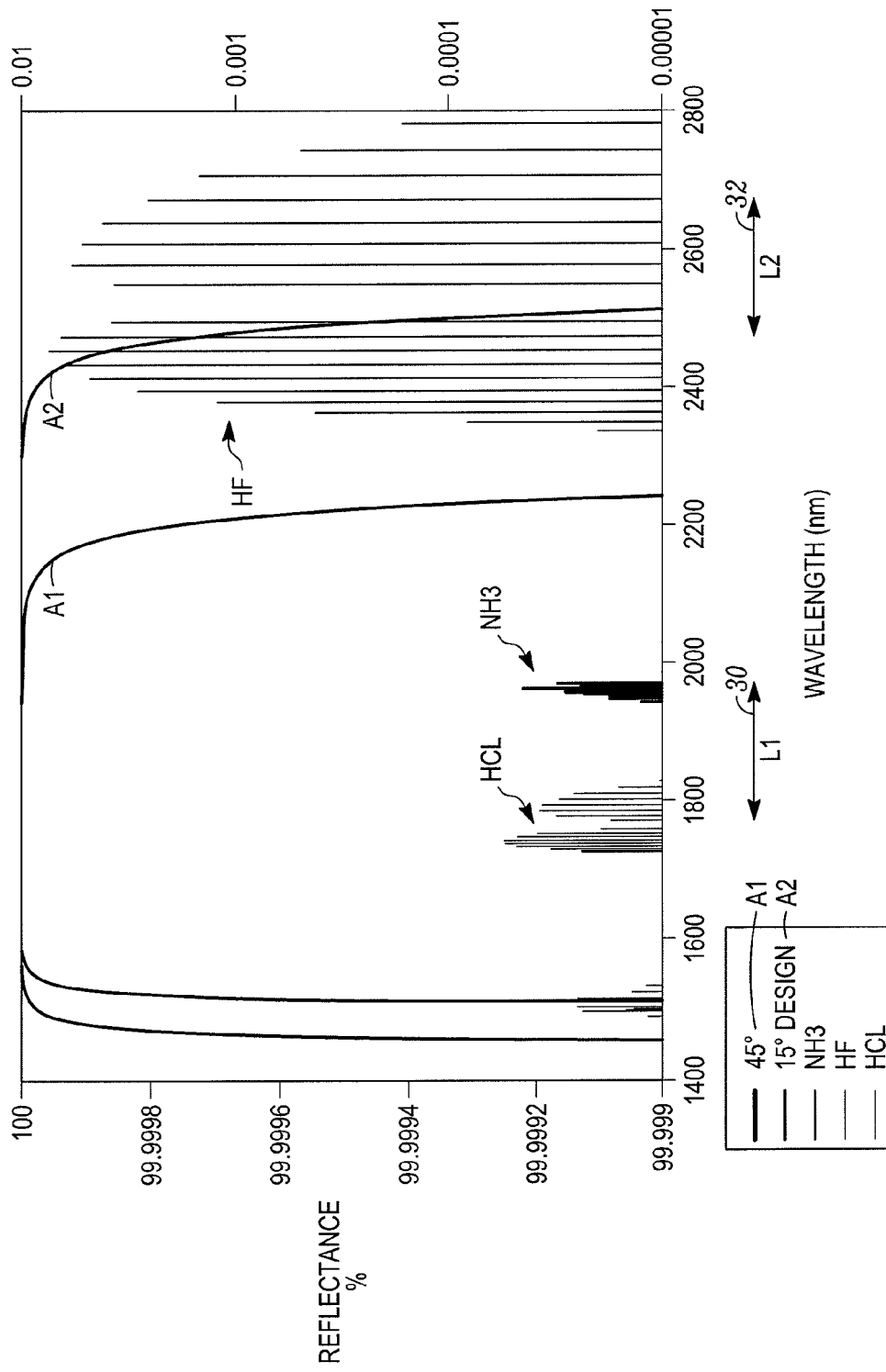
FIG. 2 is a graph illustrating characteristics of the detector of FIG. 1.

FIG. 2 illustrates additional aspects of the embodiment 10 of FIG. 1. The L1 laser, 30 has a wavelength suitable for detecting gas absorption due to either HCL or NH3 on the path P1 as the mirror 20 vibrates. In that regard, beam B1 is coupled to cavity R along path P1 and intersects the mirror 20 at angle A1, on the order of 45 degrees, relative to axis 20b where mirror 20 is in one position. Beam B2 is coupled to cavity R and circulates along path P2 and intersects mirror 20 with angle A2, on the order of 15 degrees relative to axis 20b where mirror 20 is at a second position. As a result, the two beams B1, B2 do not interfere with each other.

The embodiment 10, illustrated in FIG. 1, can be expanded with a third laser source, mirrors and an associated detector to implement a third ring that intersects mirror 20 at a location substantially common to the location of intersection of paths P1, P2. It will be understood that neither the laser wavelengths nor the specific mirror parameters are limitations of the invention.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A gas sensing device comprising:
a housing that defines an internal region through which a gas can flow; and
a piezoelectric mirror, carried by the housing where the mirror defines, at least in part more than one radiant energy transmission path through the internal region;
a first mirror pair arranged for coupling a first laser beam into the internal region via a first mirror of the first mirror pair and for reflecting by a second mirror of the first mirror pair to hit the piezoelectric mirror at a first angle; and
a second mirror pair arranged for coupling a second laser beam into the internal region via a first mirror of the second mirror pair and for reflecting by a second mirror of the second mirror pair to hit the piezoelectric mirror at a second angle different from the first angle.

2. A gas sensing device comprising:
a housing that defines an internal region through which a gas can flow; and
a piezoelectric mirror, carried by the housing where the mirror defines, at least in part more than one radiant energy transmission path through the internal region; and
at least second and third mirrors both of which are carried by the housing with all three mirrors spaced apart from one another with the piezoelectric mirror and the second mirror associated with one radiant energy transmission path, and with the piezoelectric mirror and the third mirror associated with a second, different, radiant energy transmission path.

3. A device as in claim 2 where the one radiant energy transmission path is incident on the piezoelectric mirror at a different angle than is the second radiant energy transmission path.

4. A device as in claims 2 where the piezoelectric mirror exhibits a selected curve.

5. A device as in claim 4 where a first radiant energy transmission path is incident on the piezoelectric mirror at a different angle than is a second radiant energy transmission path.

6. A device as in claim 5 where first radiant energy incident on and reflected by the piezoelectric has a first wavelength and where second radiant energy incident on and reflected by the piezoelectric mirror has a second wavelength.

7. A device as in claim 6 which includes first and second sources which emit a first radiant energy beam, at the first wavelength and a second radiant energy beam at the second wavelength.

8. A device as in claim 7 where the first and second beams are coupled into the housing by second and third mirrors spaced from the piezoelectric mirror.

9. A device as in claim 8 which includes first and second radiant energy sensors, coupled to the housing which receive radiant energy of the first and second wavelengths respectively.

10. A device as in claim 9 which includes a third source of radiant energy of a third wavelength, the third source emits radiant energy coupled into the housing to be reflected off of the piezoelectric mirror at a third, different angle than the first and second beams of radiant energy.

11. A device as in claim 10 which includes control circuits coupled to the sources, the sensors and the piezoelectric mirror to establish multiple reflecting beams within the housing, at respective wavelengths which can be detected by respective sensors and which respond to the presence of predetermined different gases in the housing.

12. A device as in claim 11 which includes at least fourth and fifth mirrors, disposed from the second and third mirrors for reflecting at least portions of incident radiant energy at the first and second wavelengths to the piezoelectric mirror and for transmitting at least portions thereof to the respective first and second sensors.

13. A device as in claim 12 where the second and third mirrors have a common curvature.

14. A method comprising:
coupling first radiant energy into a region via a first mirror of a first mirror pair;
reflecting the first radiant energy to hit a common reflective region at a first angle via a second mirror of the first mirror pair;
coupling second radiant energy into the region via a first mirror of a second mirror pair;
reflecting the second radiant energy to hit the common reflective region at a second angle, different from the first angle, via a second mirror of the second mirror pair;
altering a position parameter of the common reflective region so as to reflect the first and second radiant energy off of the common reflective region at different times.

15. A method as in claim 14 which includes moving the reflective region substantially linearly with a reciprocating motion.

16. A method as in claim 15 which includes providing the first radiant energy at a first wavelength and providing the second radiant energy at a second wavelength.

17. A method as in claim 16 which includes coupling third radiant energy of a third wavelength into the region via a first mirror of a third mirror pair, and reflecting the third radiant energy to hit the common reflective region at a third angle, different from the first and second angles, via a second mirror of the third mirror pair.

18. A method as in claim 16 which includes providing a flow of gas which intersects the first and second radiant energy.

19. A method as in claim 16 which includes obtaining indicia of at least one of the first and second radiant energy.

20. A method as in claim 19 which includes processing the indicia to establish the presence of selected gases.

* * * * *